United States Patent [19]

Swim et al.

[11] Plant 4,723

[45] May 26, 1981

[54] ROSE PLANT

[75] Inventors: Herbert C. Swim, Ontario; Arnold W. Ellis, Garden Grove, both of Calif.

[73] Assignee: Armstrong Nurseries, Inc., Ontario, Calif.

[21] Appl. No.: 110,766

[22] Filed: Jan. 9, 1980

[51] Int. Cl.[3] ..... A01H 5/00

[52] U.S. Cl. ..... Plt./26

[58] Field of Search ..... Plt./26–27

*Primary Examiner*—Robert E. Bagwill

*Attorney, Agent, or Firm*—William H. Elliott, Jr.

[57] ABSTRACT

A hybrid floribunda rose plant of the tall bush type particularly adapted for green house cultivation and having a vigorous growth habit and a tendency to bloom heavily, throughout most of the growing season. The blooms are of a two-tone deep coloration, the centers of the new blooms being of a deeper pink which accentuates their classic form. Cut flowers usually preserve their freshness for a vase life longer than average for roses of this class.

1 Drawing Figure

This invention relates to a new class of hybrid floribunda rose. The plant is a seedling of the tall bush type, cultivated primarily for cut flowers. The plant was grown in a greenhouse, and was propagated by Herbert C. Swim and Arnold W. Ellis in Ontario, Calif., having as its seed parent "Escort" (U.S. Plant Pat. No. 2,436) and as its pollen parent "Jazz Fest" (U.S. Plant Pat. No. 3,323). It holds its distinguishing characteristics through succeeding propagations by budding.

The new variety bears its flowers usually singly on normal medium to long stems, although sometimes two to three or more blooms may be carried on one stem in an irregular cluster. The plant blooms abundantly in the greenhouse and nearly continuously during the growing season. It has a slight tea fragrance.

Ways in which this new cultivar may be distinguished from its seed parent, Escort, include the following characteristics:

Escort bears red flowers, whereas the new rose bears deep pink flowers.

Escort bears significantly smaller flowers, from 2¼ to 2½ inch diameter, whereas the new rose bears flowers which are 2¾ to 3¼ inches in diameter.

The new cultivar bears significantly fewer prickles, large size only, which prickles are hooked slightly downward. Escort has both large and small prickles that are straight.

Ways in which this new cultivar may be distinguished from its pollen parent, Jazz Fest, include the following characteristics:

Jazz Fest possesses abundant quantities of stipitate glands and short white hairs on the peduncle, whereas the new rose has significantly fewer stipitate glands and no hairs.

Jazz Fest bears red flowers, whereas the new rose bears deep pink flowers.

The new cultivar has significantly more petals, from 24 to 30, than does Jazz Fest, which has from 15 to 20 petals.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

BUD

The peduncle is of average length and average caliper, being erect and with some stipitate glands. The color is between Strong Yellow Green, 5GY6/8, and Moderate Yellow Green, 5GY5/6.

Before the calyx breaks, the bud is small in size, of medium length, and pointed-ovoid in form, with small, narrow foliaceous appendages and some stipitate glands on the surface of the bud. There are usually slender foliaceous parts extending beyond the tip of the bud equal to one-half or more of its length.

As the calyx breaks, the color is near Strong Purplish Red, 7.5RP5/12.

Sepals are relatively narrow, with margins lined with stipitate glands and/or hairs.

As the first petal opens, the bud is small in size and long pointed-ovoid in form. The color of the petal, both on the inside and the outside, is between Deep Purplish Pink, 7.5RP6/12, and Strong Purplish Pink, 7.5RP7/10. The bud opens up well and is not prevented from opening by cold, hot, wet or dry weather.

BLOOM

The size of the bloom when fully open is average, ranging from 2¾ and 3¼ inches in diameter. The petalage is double, with from 24 to 30 petals arranged regularly, plus from 0 to 4 petaloids. The bloom is high centered at first, becoming cupped to high centered, the petals remaining at first somewhat tightly cupped, with tips reflexed outward, becoming later at maturity loosely cupped, with tips reflexed outward.

The petals are from medium to heavy thickness, moderately leathery, with inside slightly velvety and outside slightly shiny and satiny. The outside petals are from nearly round to very broadly obovate. Intermediate petals are broadly obovate, while inside petals are obovate in shape. The colors may be modified by being shaded and/or washed with other colors.

The paragraph immediately following describes color values observed in a flower newly opened in the month of October. The plant had been grown in a greenhouse in Ontario, Calif.

All petals, outside, intermediate and inside, were of the same coloration, the outer surfaces being between Deep Purplish Pink, 7.5RP6/12, and Strong Purplish Pink, 7.5RP7/10, while the inner surfaces were between Light Purplish Pink, 7.5RP8/5, and Strong Purplish Pink, 7.5RP7/10.

The paragraph immediately following describes the color values observed in a bloom which had been open for three days in the greenhouse, in the month of October in Ontario, Calif.

All petals, both outside and inside, were of the same coloration, the outer and inner surfaces all being between Light Purplish Pink, 5RP8/5, and Strong Purplish Pink, 5RP7/9.

The general color effect of the newly opened flower is between Strong Purplish Pink, 7.5RP7/10 and Light Purplish Pink, 7.5RP8/5. The bloom after being three days open gives a general color effect which is between Deep Purplish Pink, 7.5RP6/12, and Strong Purplish Pink, 5RP7/9. The petals drop off cleanly, except for the petaloids, and are not particularly affected by cold, hot, wet or dry weather.

Cut roses grown in the greenhouse and kept at living-room temperatures will last from 5 to 7 days in the month of December.

REPRODUCTIVE ORGANS

The stamens are average in number and arranged regularly about the pistils.

The filaments are medium length to long, most with anthers. They are near Vivid Yellow, 5Y8/12, at the base, becoming near Moderate Orange Yellow, 10YR8/10, at the point of attachment to the anthers.

Anthers are medium in size, all opening approximately at once. Their color is between Strong Orange Yellow, 10YR7/10, and Dark Orange Yellow, 10YR6/8, sometimes much lighter in color near the point of attachment to the filament.

Pollen is moderate in amount, and near Strong Orange Yellow, 10YR7/10, in color.

There are few pistils, being approximately 60 in number.

Styles are moderately even, average length and caliper, and somewhat tightly bunched. The color is pale yellow near the base and reddish near the stigma.

The stigma is near Brilliant Greenish Yellow, 10Y9/9, in color.

The ovaries are mostly enclosed in the calyx.

The hips are of average length to long, pointed and oblong, with thick fleshy walls. They are between Brilliant Yellow Green, 2.5GY9/8, and Brilliant Yellow Green, 2.5GY7/10, in color.

The sepals are permanent, medium-length to long, and curled. The inside coloration is near Strong Yellow Green, 5GY7/10, with a heavy gray bloom, while the outside is near Brilliant Yellow Green, 5GY8/8.

There are an average number of seeds, from 4 to 10, which are medium size.

FOLIAGE

The compound leaves usually comprise from three to five leaflets. They are normal in amount, medium in size, and moderately heavy. The leaflets are oval in shape, with apex mucronate, base acute, and margin doubly serrate.

The mature foliage displays upon its upper surface a color between Moderate Yellow Green, 5GY5/6, and Moderate Olive Green, 5GY4/3. The under surface is near Light Yellow Green, 7.5GY9/4.

The young foliage on its upper surface is near Dark Red, 5R3/7, in color; the under surface being near Moderate Red, 2.5R4/10, with a grayish overcast.

The rachis is average in size. The upper side is grooved with a few stipitate glands on the edges, while the under side is sparsely prickly.

The stipules are short, moderately narrow, and with short points turning out at an angle of less than 90°.

The plant displays a more than average resistance to mildew, when compared with other varieties grown under comparable conditions at Ontario, Calif.

GROWTH

The plant is of upright habit and much branched. It displays a moderately vigorous growth and has canes of light to medium caliper.

The main stems are near Brilliant Yellow Green, 2.5GY8/9, with a slight gray cast. They bear a few large prickles which are short to medium-length, hooked slightly downward, with medium-length, narrow base. The color is between gray and Strong Yellowish Brown, 7.5YR5/7. There are no small prickles and no hairs.

The branches have a color which is near Strong Yellow Green, 5GY6/8. They bear a few large prickles which are short to medium-length and hooked slightly downward, with medium-length narrow base. Their coloration is near Strong Brown, 5YR4/5. There are no small prickles and no hairs.

New shoots are between Dark Red, 5R3/7, and Dark Red, 2.5R3/7, in color. They carry a few moderately short large prickles which are hooked slightly downward, with medium-length narrow base. Their coloration is near Strong Red, 5R4/12. There are no small prickles and no hairs.

We claim:

1. A new and distinct variety of rose plant of the floribunda class, substantially as shown and described herein, and being particularly characterized by the vigor of its growth habit and the profusion of its blooms, said blooms being of a two-toned pink coloration which accentuates the classic form of the new blooms, said flowers having moderately thick heavy petals, and preserving their freshness over a vase life somewhat longer than average for roses of this class.

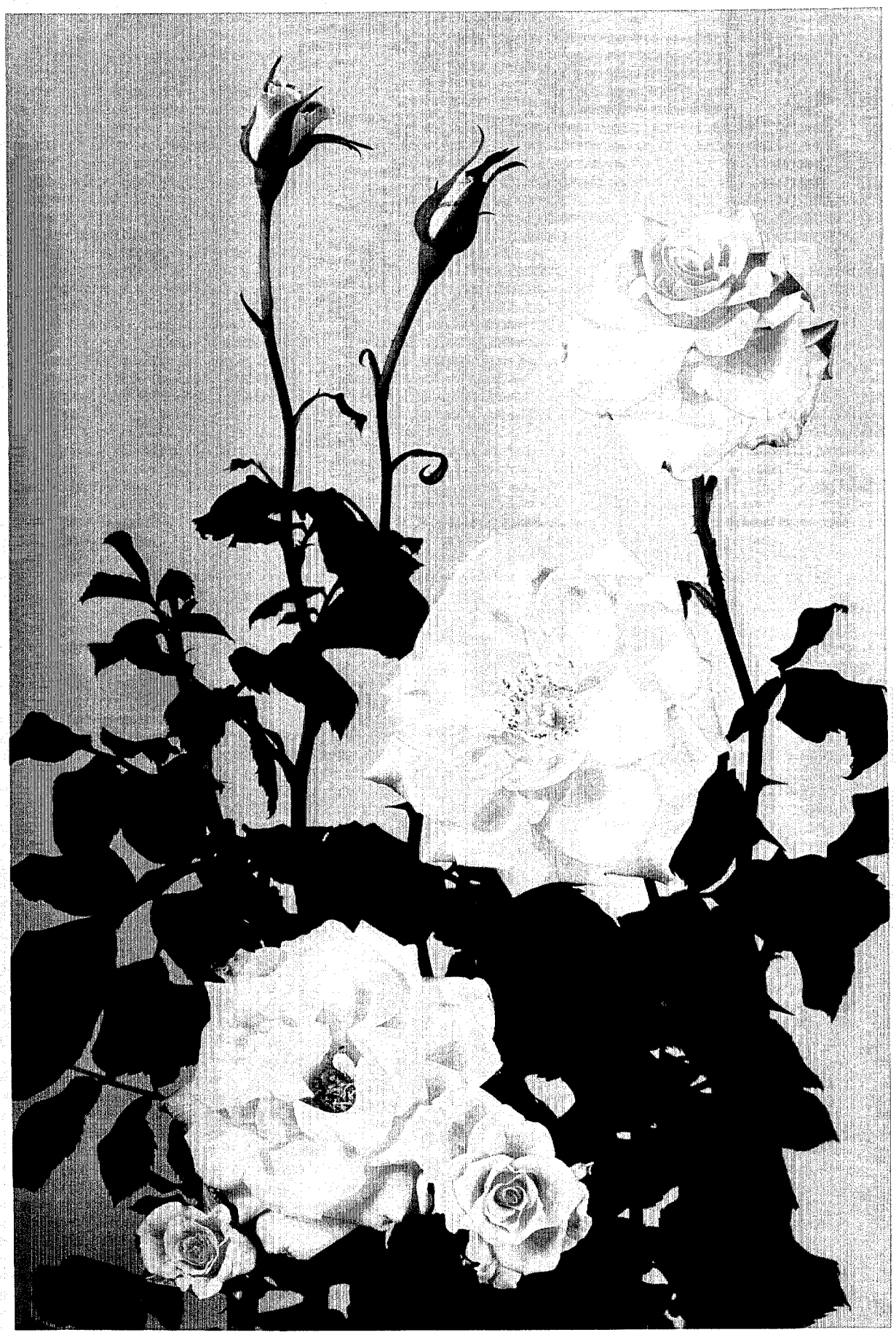

* * * * *